United States Patent
Lee

(10) Patent No.: US 7,754,245 B2
(45) Date of Patent: Jul. 13, 2010

(54) SOLID BIO-MATERIAL FOR A SENSOR THAT DETECTS BIO-ELECTRIC SIGNALS THROUGH THE USE OF THE CHARACTERISTICS AND FUNCTIONS OF BIO-EPIDERMAL TISSUES AND EPIDERMAL TISSUES OF LIVING ORGANISMS AND THE METHODS FOR PRODUCING THE SAME

(75) Inventor: Sang Moon Lee, Suite #1101, LG Twintel Bldg., 157-8 Samsung-dong, Kangnam-ku, Seoul 135-090 (KR)

(73) Assignee: Sang Moon Lee, Seoul (KR)

( * ) Notice: Subject to any disclaimer, the term of this patent is extended or adjusted under 35 U.S.C. 154(b) by 374 days.

(21) Appl. No.: 10/538,591

(22) PCT Filed: Dec. 9, 2003

(86) PCT No.: PCT/KR03/02692

§ 371 (c)(1),
(2), (4) Date: Jun. 8, 2005

(87) PCT Pub. No.: WO2004/052197

PCT Pub. Date: Jun. 24, 2004

(65) Prior Publication Data

US 2006/0029925 A1 Feb. 9, 2006

(30) Foreign Application Priority Data

Dec. 12, 2002 (KR) .................. 10-2002-0079394

(51) Int. Cl.
*A61K 35/32* (2006.01)
(52) U.S. Cl. .................................... 424/574
(58) Field of Classification Search .................. 424/574
See application file for complete search history.

(56) References Cited

U.S. PATENT DOCUMENTS 4,762,522 A * 8/1988 Maue .............. 8/94.19 R
6,913,877 B1 * 7/2005 Chaplen et al. ............ 435/4

FOREIGN PATENT DOCUMENTS

KR  1998-072300 A   11/1998
WO  WO99/27351 A    6/1999

OTHER PUBLICATIONS http://www.merriam-webster.com/dictionary/aromatic.*
Athenstaedt at al, Epidermis of human skin: pyroelectric and piezo-electric sensor layer, Science ,1982, vol. 216, Abstract.*
Elwing et al, Fish Scales as Biosensors for Catecholamines, Biosensors & Bioelectronics, vol. 5, p. 449-459, 1990.*

* cited by examiner

*Primary Examiner*—Ralph Gitomer
*Assistant Examiner*—Tiffany M Gough
(74) *Attorney, Agent, or Firm*—Joseph H. Kim; JHK Law

(57) ABSTRACT

The present invention discloses a solid bio-material for the detection of a bio-electromagnetic signal, which senses an information signal generated from living organisms and changes thereof by using fish scale, feathers of fowl and carapaces of tortoises among epidermal tissues of animals having the function of detecting, memorizing and transferring a weak information signal (bio-signal) of an electromagnetic field generated from bio-tissues, and a method for producing the same. The method for producing a solid bio-material for the detection of a bio-electromagnetic signal by using epidermal tissues of living organisms comprises the steps of: immersing the carcass of an animal with a developed epidermis such as fish, fowl, tortoises, etc. in a mixed solution of aromatics (fragrance), salt and water in the ratio of 1:2:300 for one week; separating the epidermis from the immersed living organism; washing the separated epidermis, soaking it in a mixed solution of potassium dichromate, vinegar and water in the ratio of 1:1:100 for 10 to 12 hours, applying a medium pressure thereto for 48 hours under an ambient temperature, and then drying it; applying heat of 40° C. and a cold air of −25° C. temperature in turn to the dried epidermis in a medium pressure state, two or three times in a period of 24 hours each; sterilizing the hot and cold treated epidermis by irradiating ultraviolet rays thereto with a 240 nm ultraviolet lamp for 30 minutes; generating static electricity by putting the sterilized epidermis in an electric cylinder and turning it at 500 RPM; applying pine nut oil to the outer surface of the electro statically processed epidermis; and cutting the epidermis into required sizes.

4 Claims, No Drawings

SOLID BIO-MATERIAL FOR A SENSOR THAT DETECTS BIO-ELECTRIC SIGNALS THROUGH THE USE OF THE CHARACTERISTICS AND FUNCTIONS OF BIO-EPIDERMAL TISSUES AND EPIDERMAL TISSUES OF LIVING ORGANISMS AND THE METHODS FOR PRODUCING THE SAME

TECHNICAL FIELD

The present invention discloses a solid bio-material for the detection of a bio-electromagnetic signal, which senses an information signal generated from living organisms and changes thereof by using the epidermis of living organisms, scales which have been generated from epidermis, as well as the deformation of skin which came from a degeneration or keratinization of scales, fish scales, the scales or horny substances of a reptile (tortoises)'s body surface area, the deformed body surface skin of birds and mammals, the feathers of birds (fowl), the body surface of insects, mollusca, shellfish and the cuticle on their body surfaces, vertabrata feathers or scales which contains cuticle, and the horny layer on crustacea's body surface having the function of detecting, memorizing and transferring a weak information signal (bio-signal) of an electromagnetic field generated from bio tissues, and a method for producing the same.

BACKGROUND ART

We have known about electromagnetic signals of bio-organisms since 1 BC. According to documents, the people of that period first tried to cure migraine headaches and prolapse of the anus through the use of electric fish. However, it had not been recognized as a kind of general vital phenomenon not limited to certain species until 1786 that a German biologist, physician, and anatomist, Luigi Galvani (1737-1798) observed electric potential of bio-organisms through experiments using muscles of limbs of frogs. During the experiments he observed that a limb of frog has spasms when it contacts with sparks of a electric motor or a dissecting knife and found that it is related to electricity, which made him advocate the existence of "animal electricity". Galvani's 1791 thesis made great contributions to electrophysiology, electromagnetics and electrochemistry.

Scientist Joseph Fourier a French mathematician and physicist also contributed greatly to these fields. His theory known as "Fourier Series"has allowed us to show harmonics generation that have various amplitudes and phases through frequency signals. The "Fourier Series" can be applied to biological signals such as the ECG, EEG, EMG, and GSR and refer to as "Fourier Transform".

Fourier's method for interpreting frequency of biological signal has offered us clues to the frequency range of signals and to the nature of the frequency.

German biologist Du Bois-Raymond (1818-1896) found a minute electrical current in the nervous system with very sensitive galvanometer 100 years after Galvani discovered the electric potential in a living organism.

In 1903, Dutch biologist Willem Einthoven (1860-1929), invented the first string galvanometer, known as the Einthoven galvanometer. With this instrument, he was able to measure the changes of electrical potential caused by contractions of the heart muscle and to record them graphically. He coined the term, electrocardiogram for this process.

Therefore, there have been two different methods thus far for detecting bio-signal in general. The first is passively through heat and humidity of the epidermis after adding weak electricity to the exposed epidermis. The second is actively by detecting weak electricity left on the epidermis with electrode.

However, we cannot detect the smallest differences in biological signals through either of these classical methods due to environmental changes. In other words, technology, thus far, has not been able to distinguish between the ever-slight differences of biological signals of cancer cells and other disease cells.

While searching for a more efficient material to detect the differences in the biological signals of cancer cells we discovered that the epidermis of living organisms, scales which have been generated from dermis, as well as the deformation of skin which came from a degeneration or keratinization of scales, fish scales, the scales or horny substances of a reptile (tortoises)'s body surface area, the deformed body surface skin of birds and mammals, the feathers of birds (fowl), the body surface of insects, mollusca, shellfish and the cuticle on their body surfaces, vertabrata feathers of scales which contains cuticle, and the horny layer on crustacea's body surface react very sensitively to the biological signals.

Now, let's take a closer look at the characteristics and functions of the epidermis.

We have originally believed the epidermis to be only a dead keratin tissue layer because of its lack of blood vessels, nerve endings or lymph channels. However, as technology progressed, the epidermis was found to operate a complex organ of numerous structures (sometimes called the integumentary system) serving vital protective and other functions against external (mechanical, chemical, and physical) offenses.

The ectoderm forms the whole of the nervous system, the epidermis of the skin, the lining cells of the sebaceous, sudoriferous, and mammary glands, the hairs and nails, the epithelium of the nose and adjacent air sinuses, and that of the cheeks and roof of the mouth. From it also are derived the enamel of the teeth, and the anterior lobe of the hypophysis cerebri, the epithelium of the cornea, conjunctiva, and lacrimal glands, and the neuro-epithelium of the sense organs.

When we take a look at a fish scale without its thin outer layer through a microscope, we can find many melanin crystalloids that have been formed by melanin cells when the epidermis has been formed by the ectoderm. These melanin crystalloids have a very complex structure and their shape is similar to that of Neuroglia Cells, namely, the Astrocyte and the Oligodendrocyte.

The epidermis that has been formed by the ectoderm, such as the keratin layer of the human skin, chitinous substance of insects, the epidermis of living organisms, scales which have been generated from dermis, as well as the deformation of skin which came from a degeneration or keratinization of scales, fish scales, the scales or horny substances of a reptile (tortoises)'s body surface area, the deformed body surface skin of birds and mammals, the feathers of birds (fowl), the body surface of insects, mollusca, shellfish and the cuticle on their body surfaces, vertabrata feathers or scales which contains cuticle, and the horny layer on crustacea's body surface through treatment, will be able to analyze, synthesize, memorize, learn, transform, transmit, and retransmit the electromagnetic signal spectrum of living organisms. In this way, the epidermis' function is similar to that of the human brain.

The epidermis covers the surface of the living organism with the optical medium, which is a semi-transparent, solid, intermittent multi-layer system made of mainly keratin. This intermittent multi-layer system, which has a thickness of 0.05-3 mm, has several hundred layers of semi-transparent membranes with a thickness of 10-30 Å and interval of 5-10 Å. A characteristic of this epidermal layer is its high elasticity.

This thin layer of membrane is like a microfilm and is very tight like a violin cord, with melanin crystalloid between the layers.

As the majority of all living organism, the epidermis is a polymer composed with macromolecules. In other words, the macromolecules are a long polymer chain. The monomers link up to this polymer chain in a very systematic way. The epidermal multi-layer has the same type of structure. This chain style system transforms the monomers into the polymers of living organism. The chain system of the epidermis becomes nonlinear due to the variable intensity of this chain system.

Even in the same polymers of a living organism, the expansion of the connecting area varies according to the structure of the chain system or its size.

The discrete non-linear medium with a complicated structure like the epidermis have the elements that allow for light to pass through the external electromagnetic field, disperse it and finally absorb it. The important aspect of this is that the elements allow light to pass although not in an exclusively passive way. When the bundle of light stimulates the polymer of the epidermis, its cells and monomers start to oscillate. This oscillation will be repeated several times, known as the "echo effect". This oscillating procedure will be transmitted to another polymer that will again start another echo effect.

When the outer electromagnetic field reaches the epidermis, the biopolymers of epidermis as transformers of energy, or as its oscillator, produces harmonic generation and generates an energy retransmission effect.

The oscillation harmonic generation acting like a battery instigates the initial stimulation of energy. In other words, energy becomes concentrated. In this procedure, the non-linear wave oscillation will become stable, or what we call "isolated electromagnetic wave" or known as the soliton or wave packet. This wave packet will be absorbed by the molecular resonator, which has the same oscillation characteristics as the wave packet. The reason for this is because the ability and function of the cell inside the energy filled epidermis has been controlled. The amplified electrical charge of the cell transforms the characteristics of the conformation within the cell and also modifies another biopolymer and protein molecule.

When there is interaction between light and living organism tissue, the tissue reacts to the oscillation energy information that changes according to the feedback theory. During this procedure, the characteristic of the light wave front and the characteristic of the medium that is stimulated by the absorption and penetration of light waves will be synchronized. We call this "the self-organizing effect" or the "mutual active process".

The non-linear medium, optic characteristic and multilayer system of the epidermis produce oscillation harmonic generation when the living organism like the epidermis is influenced by electromagnetic radiation.

The epidermis is very different from the other types of living organisms. The epidermis is the border between the outer and inner environments however; the epidermis is also the medium that connects the two environments together. Thus, we can refer to the epidermis of living organisms, scales which have been generated from dermis, as well as the deformation of skin which came from a degeneration or keratinization of scales, fish scales, the scales or horny substances of a reptile (tortoises)'s body surface area, the deformed body surface skin of birds and mammals, the feathers of birds (fowl), the body surface of insects, mollusca, shellfish and the cuticle on their body surfaces, vertabrata feathers or scales which contains cuticle, and the horny layer on crustacea's body surface as "multi-information systems".

The epidermis will not simply allow all types of light spectrum, from ultraviolet rays to near infrared rays, to pass through. The epidermis is very selective in what it will allow to pass through and will generate a drastic change in some areas of the spectrum. This is the result of the resonance of the epidermis.

The epidermis will absorb the radiated energy from the electromagnetic field after being stimulated. However, this is not simple absorption but a modifying procedure of the spectrum of radiated energy. From a biological point of view, this is of great significance. When the radiated spectrum is transferred to short-wave range, excess energy will be generated within the living organism. In other words, the core energy that enhances the activity of the living organism is as such produced.

The radiated quantum that is measured by the unit of photon is proportional to V(frequency waves; $E\Phi=h\nu_0$). As the wavelengths $\lambda(\lambda=c/\nu$, c=speed of light in the vibration) shortens, the frequency and photon energy increase. In fact, the numerical value of photon energy $E\Phi^1=h\nu_0^1$ (h=Planck's constant) changes. The difference between the "re-radiated" photon energy and the initial photon energy $(\Delta E\Phi=h\nu_0^1 - h\nu_0 = h(\nu_0^1-\nu_0)=h\Delta\nu)$ will be used for the metabolism of the living organism. When the living organism is placed under light, light waves are converted to energy. One type of energy is for metabolism and another type is for other purposes.

The epidermis is a non-linear multilayer optic medium that has similar functions as the brain. The epidermal oscillators interact with each other despite its connecting system that looks non-linear, harmonious, and immobile. In consequence, even the smallest stimulation can generate various physical changes such as mechanical, optical, and electric oscillations on the epidermal surface structure. When the epidermis is exposed to any type electromagnetic field from an unhealthy living organism, many mechanical, optical, and electric oscillations will be generated on the multilayers within the epidermis. The interpretation of these three oscillations allows us to conclude that our treated epidermis can analysis and synthesis the nature of the electromagnetic field from the unhealthy living organism.

The epidermis contains trace amounts of electrolytes. The thin epidermal layer is composed of a very solid layer system. And, in view of electrophysics, the epidermis is almost same as an insulator having $10^{12} \sim 10^{15}$ ohm. However, the epidermis belongs to the bio-electret under certain conditions. In this case, the bio-electret is the dielectric substance with quasiconstant electric charges. All types of electret charges are very stable. We can observe this electret effect in the biopolymer. The epidermis, which is a biopolymer, optic multi-layer medium, and keratin thin layer, is a natural bio-electret that reacts by generating electric oscillation from the stimulation of an outer electromagnetic field.

The epidermis is a non-linear medium. Since the dielectric constant of non-linear medium is sensitive to the electromagnetic field, the epidermis exposed to a very strong electromagnetic field can generate polarization. Furthermore, this bio-electret can retain polarization even after being removed from the source of polarization.

Even piezoelectricity has been observed on the epidermis. Its characteristics are to be authentic ferroelectrics so that the epidermis is considered "semi-stable ferroelectrics".

The ferroelectrics exposed to the very strong electromagnetic field has a different non-linear relationship of polarization according to the intensity of the outer electromagnetic field; in consequence, harmonic generation is produced in the electric current that is passed through the dielectric like the epidermis.

The epidermal thin multilayer contains keratinocyte generated from the ectoderm. In general, the micro molecules of a cell like the nucleocyte, porphyrin, flavin, quinnone, amino acids, and kerotinoid have something in common. Compared to most organic compounds, the micro molecule of a cell has low-electrical stimulated energy, low ionized potential, high electronic affinity, and high electronic polarization. In consequence, the main polarization mechanism generated on the epidermis is electronic polarization.

The epidermis is a dielectric crystalloid. The melanin in the epidermal structure is evidence of this. The characteristics of the internal epidermal crystalloid are influenced by the electromagnetic field, especially by the electromagnetic wave of the radiated energy change. Its refraction value changes too. In some crystalloids, the polarization constant changes in proportion to the multiplication of the electric field. In this case, the crystalloid has a linear electro-optic effect. All types of crystalloids of the dielectrics theoretically should retain the electro-optic effect of the Square, which means an increase of the progression of the polarization constant in proportion to the Square of the electric field. The epidermis is a non-linear optic crystalloid dielectric that generates the polarization by the influence of the external electromagnetic field.

Let's proceed to the mathematical procedure for non-linear polarization. The non-linear optic effect shows how the dielectric rate changes according to the intensity of the light wave increasing within the medium. The vector of the electric intensity of the electromagnetic field radiated by the light wave could be formulated as the following:

$$\vec{E}(\vec{r},t) = 1/2 \vec{e} \{A(\vec{r},t)\exp[i(\omega t - \vec{k}\vec{r})] + k.c.\} \quad (1)$$

In this case, $\vec{e}$ is a simple vector of the polarization. $\vec{A}(r,t)$ is the Complex Amplitude of the light wave. k.c. is a Complex Conjugated Component.

The multiplier that changes with the independent variable $\vec{A}(r,t)$ takes more time to change, comparing with multiplier $\exp[i(\omega t - \vec{k}\vec{r})]$. Thus, we can get the following inequality:

$$\frac{\partial A}{\partial t} \cdot \frac{1}{\omega} \ll A; \quad \frac{\partial A}{\partial \vec{r}} \cdot \frac{1}{\vec{k}} \ll A_{NL}. \quad (2)$$

In this case, the equation $A(\vec{r},t)$ is an integral number that has the distance of $2\pi/k = \lambda$, and has a time difference of $1/\omega$.

k.c., the Complex Conjugated Component of formula (1) is worth noticing because the substantiality of the intensity of the electric field can be retained by it. The complex formula $\vec{E} = \vec{e} A \exp[i(\omega t - \vec{k}\vec{r})]$ shows the intensity of the electric field cannot be applied in the non-linear theory but in the linear theory.

In the linear equation, Re $\vec{E}$, Im $\vec{E}$ are independent. However, if the non-linear terms like $E^2$, $E^3$ are involved, ReE and ImE begin to have a reciprocal relationship. As a result, a real number like the electric field intensity should be applied in the non-linear theory.

All the non-linear optic phenomena that exist on earth have the same origin despite their diversity. All non-linear optic phenomena are a result of non-linear polarization {real number and the mantissa of non-linear characteristics} of the medium.

Let's take a look at a phenomenon that has a relationship with a real number that displays the characteristics of the Square.

For example, supposing that the light wave of the frequency wave ω penetrates the square non-linear dielectric substance. In this case, we suppose that the intensity of the field of wave is like formula (1). If we apply formula (1) to show the square polarization vector, then we apply the formula of the conditional vector $$P_{sqi} = \sum_{k=1}^{3}\sum_{j=1}^{3} x_{ikj} E_k E_j$$

and will get the following formula:

$$\vec{P}_{sq} = 1/4x : \vec{e}\vec{e}\{A\exp[i(\omega t - \vec{k}\vec{r})] + k.c.\}^2 \quad (3)$$
$$= 1/4x : \vec{e}\vec{e}\{A\exp[i(2\omega t - 2\vec{k}\vec{r})] +$$
$$A^{*2}\exp[i(2\vec{k}\vec{r} - 2\omega t)]\} + 2AA^*$$

The two augends of formula (3) show the wave of polarization at the frequency wave 2ω, the third element is related to Optic Rectification. The wave of polarization of frequency wave 2 will be re-radiated at the same frequency wave under the proper conditions. In other words, the second optic harmonic generation of the frequency wave of 2 is produced in the medium.

The square non-linear medium like the epidermis concentrates the wave frequency spectrum when the light wave disperses on the inside. And when the two waves react reciprocally on the standard frequency, the re-radiated wave of the frequency wave 2 is generated. This is the second optic harmonics generation.

This is how the non-linear optic medium in the form of the crystalloid produces the second harmonics generation. The epidermis is a crystalloid including a melanin corpuscle.

The epidermis has a Periodic System after which the two layers next to each other can be distinguished by the different physical characteristics like the dielectric and this difference is transferred from one layer to the other several times.

When we examine the epidermis of living organisms, scales which have been generated from dermis, as well as the deformation of skin which came from a degeneration or keratinization of scales, fish scales, the scales or horny substances of a reptile(tortoises)'s body surface area, the deformed body surface skin of birds and mammals, the feathers of birds (fowl), the body surface of insects, mollusca, shellfish and the cuticle on their body surfaces, vertabrata feathers or scales which contains cuticle, and the horny layer on crustacea's body surface through the microscope, we can observe hundreds of epidermal layers juxtaposed in the micron unit of periodicity.

The two epidermises next to each other in the periodic system have different optico-physical characteristics. First, the refractive values n, n', to two different dielectric constant rates $\in$, $\in'$ are different. The non-linear way the optic harmonic generation is produced is also a characteristic of the periodic medium.

The original characteristic of the periodic medium is that the condition of synchronization is modified when harmonic generation is produced. The diffraction of the harmonic generation derived from the non-linear periodic medium emphasizes the non-linear optic modifying effect. In other words, the periodic medium like the epidermis has optimal conditions for phase synchronization and harmonic generation.

The incidence angle range of the bundle of scattered light is wide enough for all types of angles for synchronization. In other words, a general type of lighting can generate phase synchronization even on the epidermal multi-layer structure of the living organism.

The sun energy in range of infrared reaching the earth can influence all types of living organisms while some of this sun energy is reflected on the epidermis. Sometimes, the sun energy is refracted, scattered and finally absorbed on the border of the dielectric layer. The very active non-linear optic medium like the epidermis modifies and shortens the outer energy/infrared light inside of the epidermis.

When multiple monochromatic waves are diffused on the epidermis, its non-linearity generates a combined frequency. The amplitude of each combining wave defines its amplitude. Even if even one of the combining frequencies stays in the visible diapason, the combined frequency will equally remain there. Because only the first combining wave determines the output, despite the fact that there are an enormous number of existing combining waves, outer radiation could be relatively strong contrary to its weak input signal.

In this way, the choice of the form of phase front can visualize not only electromagnetic signals but also the shape of the object. In other words, the epidermis can modify the infrared radiation through a non-linear optic process. But it is important to notice that the non-linear optic modifier like the epidermis can also preserve the information about the phase structure of infrared radiation.

The epidermis, which is constantly open to external stimulation, is a discrete non-linear multilayer system that continuously deals with the information from the outer environment. This type of system generates a spontaneous wave process. This is the self-surviving and self-retaining process of the wave within the very active non-linear medium. This process can retain the characteristics of the wave process such as wavelength, speed of expansion, wave-width, and wave-shape due to the inner natural energy of the multilayer.

As discussed above, because the epidermis is simultaneously open to all types of outer stimulations, the epidermal layer exposed on outer electromagnetic field is "strongly influenced." As soon as the living electromagnetic signal reaches the epidermal layer, the epidermis reacts very sensitively. We then can observe this by the numerical optico-electrical value. This is how the epidermis analyzes and synthesizes the signal of the living organism.

DISCLOSURE OF THE INVENTION

As we have just discussed, our invention is the manufacturing of a solid bio-material with the characteristics of the epidermis by separating the epidermal tissue from a living organism. The characteristics of the epidermis allow us to detect cancer cells by distinguishing signals between cancer cells and normal healthy cells. The characteristics of the epidermis also allow us to produce a more efficient fertilizer.

Thus, the purpose of our invention is to create bio-materials for the use in the production of a bio-sensor and the process of manufacturing the bio-sensor.

BEST MODES FOR CARRYING OUT THE INVENTION

The object of our invention is a solid bio-material for the detection of a bio-electromagnetic signal by using epidermal tissues of living organisms by the method of: immersing the carcass of the living organism with the epidermis of living organisms, scales which have been generated from dermis, as well as the deformation of skin which came from a degeneration or keratinization of scales, fish scales, the scales or horny substances of a reptile(tortoises)'s body surface area, the deformed body surface skin of birds and mammals, the feathers of birds(fowl), the body surface of insects, mollusca, shellfish and the cuticle on their body surfaces, vertabrata feathers or scales which contains cuticle, and the horny layer on crustacea's body surface, etc. in a mixed solution of aromatics (fragrance), salt and water; separating the epidermis from the immersed living organism; washing the separated epidermis, soaking it in a mixed solution of potassium dichromate, vinegar and water, and then drying it in room temperature; applying hot and cold air in turn to the dried epidermis, sterilizing the hot and cold treated epidermis by irradiating ultraviolet rays; generating static electricity; selecting areas with concentrated melanin crystalloid; cutting the epidermis into required sizes and applying pine nut oil to the outer surface. We then take these solid bio-materials for a sensor that detects bio-electric signals.

Let's take a detailed look at the methods for producing the solid bio-material for the detection of a bio-electromagnetic signal by using epidermal tissues of living organisms by: immersing the carcass of the living organism with the epidermis of living organisms, scales which have been generated from dermis, as well as the deformation of skin which came from a degeneration or keratinization of scales, fish scales, the scales or horny substances of a reptile(tortoises)'s body surface area, the deformed body surface skin of birds and mammals, the feathers of birds(fowl), the body surface of insects, mollusca, shellfish and the cuticle on their body surfaces, vertabrata feathers or scales which contains cuticle, and the horny layer on crustacea's body surface, etc. in a mixed solution of aromatics (fragrance), salt and water in the ratio of 1:2:300 for one week; the water temperature should range between 25-27° C.

The reason for the immersion is to accelerate the decomposition of the carcass that will allow for an easier separation of the epidermis and for the minimalization of scarring on the epidermis.

For maximum melanin crystalloid, the epidermis should be thick and semi-transparent. Semi-transparency is necessary for the optical function of the epidermis while the thickness will allow for an easier creation of harmonic generation energy.

The separating procedure is as follows: the immersed the epidermis of living organisms, scales which have been generated from dermis, as well as the deformation of skin which came from a degeneration or keratinization of scales, fish scales, the scales or horny substances of a reptile (tortoises)'s body surface area, the deformed body surface skin of birds and mammals, the feathers of birds (fowl), the body surface of insects, mollusca, shellfish and the cuticle on their body surfaces, vertabrata feathers or scales which contains cuticle, and the horny layer on crustacea's body surface should be separated from the decomposed living organism by carefully peeling with pincet; washing the separated epidermis in warm water by rubbing epidermis with a soft sponge; soaking it in a mixed solution of potassium dichromate, vinegar and water (for purification and softening) in the ratio of 1:1:100 for 10 to 12 hours at room temperature (18-20° C.); applying a medium pressure thereto for 48 hours in room temperature to prevent deformation.

When the above procedures are completed and the epidermis is dry, the procedure is as follows: apply heat of 40° C. and cold air of −25° C. temperature in turn to the dried epidermis in a medium pressure state, two or three times in a period of 24 hours each; sterilize the hot and cold treated epidermis by irradiating ultraviolet rays thereto with a 240 nm ultraviolet lamp for 30 minutes; generate static electricity by putting the sterilized epidermis in an electric cylinder and turning it at 500 RPM to further activate oscillation; a thin soft fabric cover must be applied over the epidermis during the static electricity generation process to prevent damage; apply pine oil to the outer surface of the electro statically processed epidermis; and cut the epidermis into required sizes. The reason for applying pine nut is to prevent humidity from occurring on the surface of the epidermis.

This new biological material made through the just mentioned manufacturing procedure becomes a non-linear optical epidermal tissue that has a semi-transparent, multilayer structure and melanin crystalloid. This material can produce various optical, physical, and electrical phenomena such as a non-linear echo effect while the external electromagnetic spectrum is penetrating it. This new material now can also detect, analyze, synthesize, memorize, transform and transmit electromagnetic signals from the external environment. In consequence, even after separating from the organism, our method enhances the epidermis' ability to react to or create energy. Our new material will be the perfect medium for the detection of diseases and/or the fertilization of soil. These results will have lasting effects.

Here are the main characteristics of the epidermis that may be used for several purposes.

1) Optical Characteristics

1. Epidermal layer of the living organism reacts very actively and sensitively to electromagnetic radiation.

2. Quantum energy forms on the epidermal layer that has been exposed to radiation because the epidermis is discrete non-linear multilayer optic medium. In consequence, the epidermal layer reacts like a laser causing oscillation harmony to occur.

3. When receiving electromagnetic radiation from a bio-object, the epidermis, because it is a non-linear multilayer optic medium and an oscillator (multilayer of membrane, melanin crystalloid, etc.), experiences mutual internal reactions.

4. The electromagnetic oscillation that occurs on the epidermal layer by the influence of the electromagnetic radiation moves, following the periodic structure of the epidermis.

5. The collision between the epidermis, which is a non-linear optical medium, and many electromagnetic light waves, creates optical oscillation which in turn creates harmonic generation 6. The expansion of the light wave from the non-linear optic medium creates the concentration of the frequency spectrum and transposes the electromagnetic spectrum and shortens the wavelengths.

7. The intervals of the membrane layers of the epidermis cause the changes in the Light System under the influence of the electromagnetic radiation and causes Harmonic Generation.

8. The non-linear crystalloid of the epidermis such as a melanin corpuscle is the main medium that creates the second Harmonic Generation.

2) Physical Characteristics

1. The non-linear oscillator of the epidermis (thin layer, melanin crystalloid, biopolymer, etc.), which has been exposed to the electromagnetic spectrum, creates physical oscillation.

2. The non-linear oscillators of the epidermis transform the electromagnetic spectrum, create energy, and retransmit energy.

3. The multilayers of the epidermis, which have different physical characteristics as periodic mediums, cause non-linear harmonic generation.

4. When the periodic medium, like the epidermis, reaches the zero wave transformation, which is the necessary condition for phase synchronization, harmonic generation occurs.

5. The diffraction of the first harmonic generation generates many non-linear optic effects of the frequency due to the multilayer structure of the epidermis. The approaching of the waves to the inner space cycle of the medium creates the second harmonic generation.

6. The multilayer, discrete nonlinear medium like the epidermis generates spontaneous electromagnetic oscillation phenomenon.

7. The non-linear optic medium like the epidermis generates a harmonic generation due to the various light waves exchanging energy.

8. A shortened electromagnetic spectrum wave on the epidermis creates extra energy that further stimulates activities in the inner body of the living organism. In this case, the amount of the generated energy can be calculated by an algebraic equation.

9. The keratin of the epidermis allows the living organism to receive a greater amount of information and retain homeostasis. The epidermis can play the role of the very complicated infomatical, optico-physical, and electrical medium that shows the very active medium between the inner and outer environments. The epidermis can also play the very important role as the energy supplying system of the living organism and can control the relationship with another living organism.

3) Electrical Characteristics

1. The external electromagnetic spectrum can transform the epidermis, which is close to an insulator having electric resistance of $10^{12} \sim 10^{15} \Omega$ to a Dielectric Substance conducting polarization.

2. The keratinocyte of the epidermis causes non-linear electromagnetic polarization under the influence of electromagnetic spectrum.

3. The epidermis is the bio-electret, which can retain polarization even without the external primary source of polarization.

4. The bio-electret that has been influenced by the electromagnetic field produces Harmonic Generation due to the changes of the non-linear relationship of polarization.

As shown above, the optical, physical and electrical characteristics of the micro multilayer epidermal becomes dramatically active through our biosensor manufacturing procedure after separating from the organism.

The followings examples show specific application of the solid bio materials for the detection of bio-signal using epidermal tissues of living organism according to the present invention may be applied to the following fields.

First, in the case of the reaction of the biosensor to energy of living organisms, our solid living bio-material can detect, analyze, and synthesize the electromagnetic spectrum of living organisms that have abnormal cells such as cancer or tumor cells. So, if we set up this solid living bio-material on the head of the probe, the solid living bio-material will detect and amplify even the smallest capacitance from the living organism. Our probe is equipped with three special circuits; the first circuit enables the probe to amplify and transform this capacitance into frequency waves; the second enables the probe to take the frequency waves and diagnose them; the third enables the probe to transform the diagnoses and translate it into digital form, which is displayed on an LCD panel.

Second, in the case of the fertilizing aspect of the solid living bio-material, it can rejuvenate soil and aid in the growth of crops and plants. For this purpose, we utilized bird feathers. The solid living bio-material treated through our procedure can revive uncultivable soil by stimulating the solid living organism in soil and enhancing growth of crops and plants.

In order to test for the fertilization purpose of our solid living bio-material, we sowed barley seeds in 1) soil mixed with invented solid living bio-material and 2) soil mixed with non-treated bird feather.

Note: All conditions were held constant between two soil tests and results were taken three days after disseminating seeds.

| | | Unit: cm |
|---|---|---|
| | The growth rate of barley grown in soil mixed with | |
| | invented solid living organism sample (treated) | non-treated bird feathers |
| 3 days after disseminating seeds in soil | 0.2 | — |
| 4 days | 4 | 1 |
| 5 days | 6 | 2.4 |
| 6 days | 10.1 | 5 |
| 7 days | 14 | 7 |
| 8 days | 18 | 9.5 |
| 9 days | 20 | 13.5 |
| 10 days | 20 | 14 |
| 11 days | 19.5 | 14 |
| 12 days | 21 | 14 |
| 13 days | 21.75 | 14.5 |
| 14 days | 23 | 15 |
| 15 days | 24 | 16 |
| 16 days | 24.5 | 17 |
| 17 days | 25.5 | 17.5 |
| 18 days | 26 | 18 |
| 19 days | 27 | 18.5 |
| 20 days | 27.5 | 19.5 |
| 21 days | 29 | 20.5 |
| 22 days | 30 | 21 |
| 23 days | 30 | 22 |
| 24 days | 32 | 22.5 |
| 25 days | 33 | 24 |

According to the above results, we found that barley seeds strewn in soil mixed with invented solid living organism grew at a much faster rate than barley seed strewn in soil mixed with non-treated bird feathers.

INDUSTRIAL APPLICABILITY

This invention gives us the new biological materials in order to enhance human life. The biological materials may be used for detecting cancer or creating a revolutionary fertilizer. The new materials are made of the epidermis of living organisms, scales which have been generated from dermis, as well as the deformation of skin which came from a degeneration or keratinization of scales, fish scales, the scales or horny substances of a reptile (tortoises)'s body surface area, the deformed body surface skin of birds and mammals, the feathers of birds (fowl), the body surface of insects, mollusca, shellfish and the cuticle on their body surfaces, vertabrata feathers or scales which contains cuticle, and the horny layer on crustacea's body surface which can detect, analyze, synthesize, memorize, transform and transmit electric charges from the skin.

The invention claimed is:

1. A method of manufacturing a solid bio-material for the detection of an electromagnetic signal by using developed epidermal tissue separated from an organism, said method comprising:
    immersing the organism selected from the group consisting of fish, fowl, and tortoises in a mixed solution of fragrances, salt and water in the ratio of 1:2:300 for one week;
    separating the epidermis from the immersed organism to form a separated epidermis;
    washing said separated epidermis to form a washed epidermis;
    soaking said washed epidermis in a mixed solution of potassium dichromate, vinegar and water in the ratio of 1:1:100 for 10 to 12 hours to form a soaked epidermis;
    drying said soaked epidermis at room temperature to form a dried epidermis;
    applying heat of 40° C. and then cold air of −25° C. temperature to said dried epidermis two or three times in a 24-hour period to form a heated and cooled epidermis;
    irradiating said heated and cooled epidermis with ultraviolet rays using a 240 nm ultraviolet lamp for 30 minutes to form an irradiated epidermis;
    rotating said irradiated epidermis at 500 RPM to generate static electricity to form a rotated epidermis;
    applying pine nut oil to the outer surface of said rotated epidermis to form an oiled epidermis; and
    cutting said oiled epidermis into required sizes, to fit the head of a probe,
    wherein said bio-material senses electromagnetic signals in a detectable manner.

2. The method of claim 1 wherein the bio-material is epidermis selected to contain concentrated melanin crystalloid.

3. The method of claim 2 wherein the epidermis is oiled epidermis.

4. A method of manufacturing a solid bio-material for the detection of an electromagnetic signal by using developed epidermal tissue separated from an organism, said method consisting of:
    immersing the organism selected from the group consisting of fish, fowl, and tortoises in a mixed solution of fragrances, salt and water in the ratio of 1:2:300 for one week;
    separating the epidermis from the immersed organism to form a separated epidermis;
    washing said separated epidermis to form a washed epidermis;
    soaking said washed epidermis in a mixed solution of potassium dichromate, vinegar and water in the ratio of 1:1:100 for 10 to 12 hours to form a soaked epidermis;
    drying said soaked epidermis at room temperature to form a dried epidermis;
    applying heat of 40° C. and then cold air of −25° C. temperature to said dried epidermis two or three times in a 24-hour period to form a heated and cooled epidermis;
    irradiating said heated and cooled epidermis with ultraviolet rays using a 240 nm ultraviolet lamp for 30 minutes to form an irradiated epidermis;
    rotating said irradiated epidermis at 500 RPM to generate static electricity to form a rotated epidermis;

applying pine nut oil to the outer surface of said rotated epidermis to form an oiled epidermis; and cutting said oiled epidermis into required sizes, to fit the head of a probe, wherein said bio-material senses electromagnetic signals in a detectable manner.

* * * * *